United States Patent
Hwang

(10) Patent No.: US 10,551,925 B2
(45) Date of Patent: Feb. 4, 2020

(54) METHOD AND APPARATUS FOR GENERATING TACTILE SENSATION

(71) Applicant: Electronics and Telecommunications Research Institute, Daejeon (KR)

(72) Inventor: In Wook Hwang, Sejong-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 121 days.

(21) Appl. No.: 15/815,027

(22) Filed: Nov. 16, 2017

(65) Prior Publication Data
US 2018/0143690 A1    May 24, 2018

(30) Foreign Application Priority Data
Nov. 21, 2016   (KR) .................... 10-2016-0155076

(51) Int. Cl.
*G06F 3/01*     (2006.01)
*G06F 3/0488*   (2013.01)
*G01N 29/34*    (2006.01)

(52) U.S. Cl.
CPC .......... *G06F 3/016* (2013.01); *G01N 29/346* (2013.01); *G01N 29/348* (2013.01); *G06F 3/0488* (2013.01)

(58) Field of Classification Search
CPC .... G01N 29/346; G01N 29/348; G06F 3/016; G06F 3/0416; G06F 3/04817; G06F 3/03547; G06F 3/04845; G06F 3/18; G06F 3/04883; G06F 3/0488
See application file for complete search history.

(56) References Cited

U.S. PATENT DOCUMENTS

| 6,747,631 | B1 * | 6/2004 | Sakamaki ................. G01L 1/14 345/157 |
| 8,451,248 | B1 * | 5/2013 | Kim ........................ G06F 3/016 345/173 |
| 8,560,976 | B1 * | 10/2013 | Kim ................. H04N 21/42228 715/702 |

(Continued)

FOREIGN PATENT DOCUMENTS

| KR | 1020130112196 A | 10/2013 |
| KR | 101485591 B1 | 1/2015 |

OTHER PUBLICATIONS

Inwook Hwang et al., An Improved Method for Generating Multiple Focuses in Non-contact Ultrasonic Haptic Display, 2016, pp. 831-833, Realistic Broadcasting Media Research Department, Electronics and Telecommunications Research Institute, Daejeon, Republic of Korea.

(Continued)

*Primary Examiner* — Helen C Kwok
(74) *Attorney, Agent, or Firm* — William Park & Associates Ltd.

(57) ABSTRACT

Disclosed are a method and an apparatus for generating a tactile sensation. The method of generating the tactile sensation according to an embodiment of the present disclosure may include: determining a tactile sensation information; generating wave signals associated with each tactile sensation information; generating ultrasonic driving signals in which phases and output timings of the wave signals are adjusted based on frequencies and a number of the wave signals; and generating the tactile sensation associated with the ultrasonic driving signals.

20 Claims, 8 Drawing Sheets

(56) References Cited

U.S. PATENT DOCUMENTS

| | | | |
|---|---|---|---|
| 8,823,603 B1 * | 9/2014 | Kim | G06F 3/016 345/156 |
| 9,265,974 B2 | 2/2016 | You et al. | |
| 10,281,567 B2 * | 5/2019 | Carter | G01S 7/52004 |
| 2009/0058829 A1 * | 3/2009 | Kim | G06F 3/016 345/173 |
| 2010/0156822 A1 * | 6/2010 | Lee | G06F 3/016 345/173 |
| 2010/0270089 A1 | 10/2010 | Kyung et al. | |
| 2011/0032088 A1 | 2/2011 | Kim et al. | |
| 2013/0265226 A1 * | 10/2013 | Park | G06F 3/017 345/156 |
| 2014/0085221 A1 * | 3/2014 | Kim | G06F 3/016 345/173 |
| 2014/0240245 A1 * | 8/2014 | Kim | G06F 3/016 345/173 |
| 2015/0062024 A1 * | 3/2015 | Kim | G06F 3/0488 345/173 |
| 2015/0091818 A1 * | 4/2015 | Kim | G06F 3/016 345/173 |
| 2015/0192995 A1 * | 7/2015 | Subramanian | G06F 3/016 340/407.1 |
| 2015/0251025 A1 * | 9/2015 | You | A61N 7/00 601/2 |
| 2017/0097682 A1 * | 4/2017 | Endo | G06F 3/016 |
| 2017/0115734 A1 * | 4/2017 | Shimotani | G06F 3/016 340/407.1 |
| 2017/0123499 A1 * | 5/2017 | Eid | G06F 3/016 |
| 2017/0139479 A1 * | 5/2017 | Shimotani | G06F 3/016 |
| 2017/0262060 A1 * | 9/2017 | Katsuki | G06F 3/016 345/173 |
| 2018/0088698 A1 * | 3/2018 | Suzuki | G06F 3/016 345/173 |

OTHER PUBLICATIONS

Tom Carter et al., UltraHaptics: Multi-Point Mid-Air Haptic Feedback for Touch Surfaces, Oct. 8-11, 2013, pp. 505-514, Department of Computer Science and Department of Mechanical Engineering, University of Bristol, ACM, St Andrews, United Kingdom.

* cited by examiner

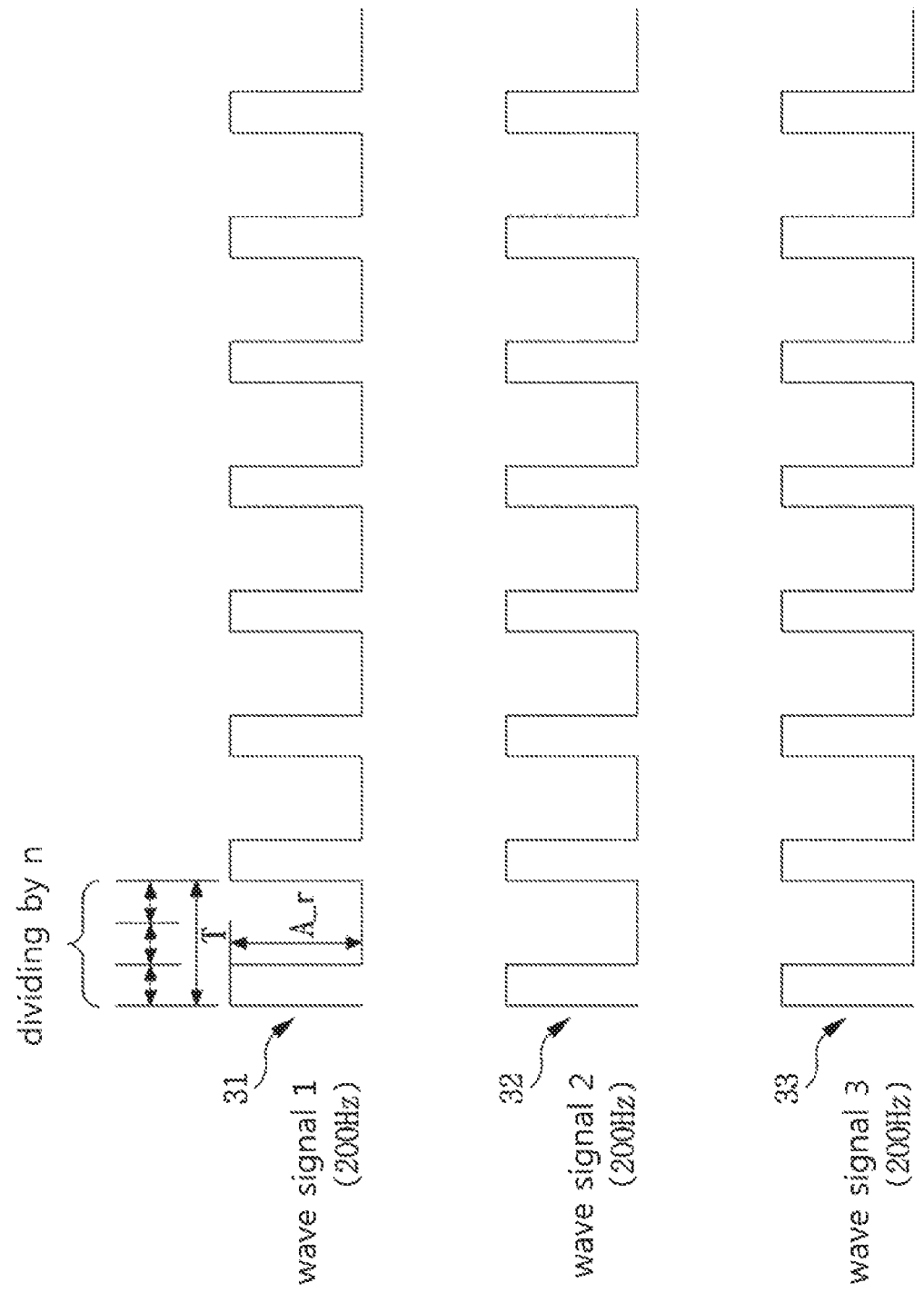

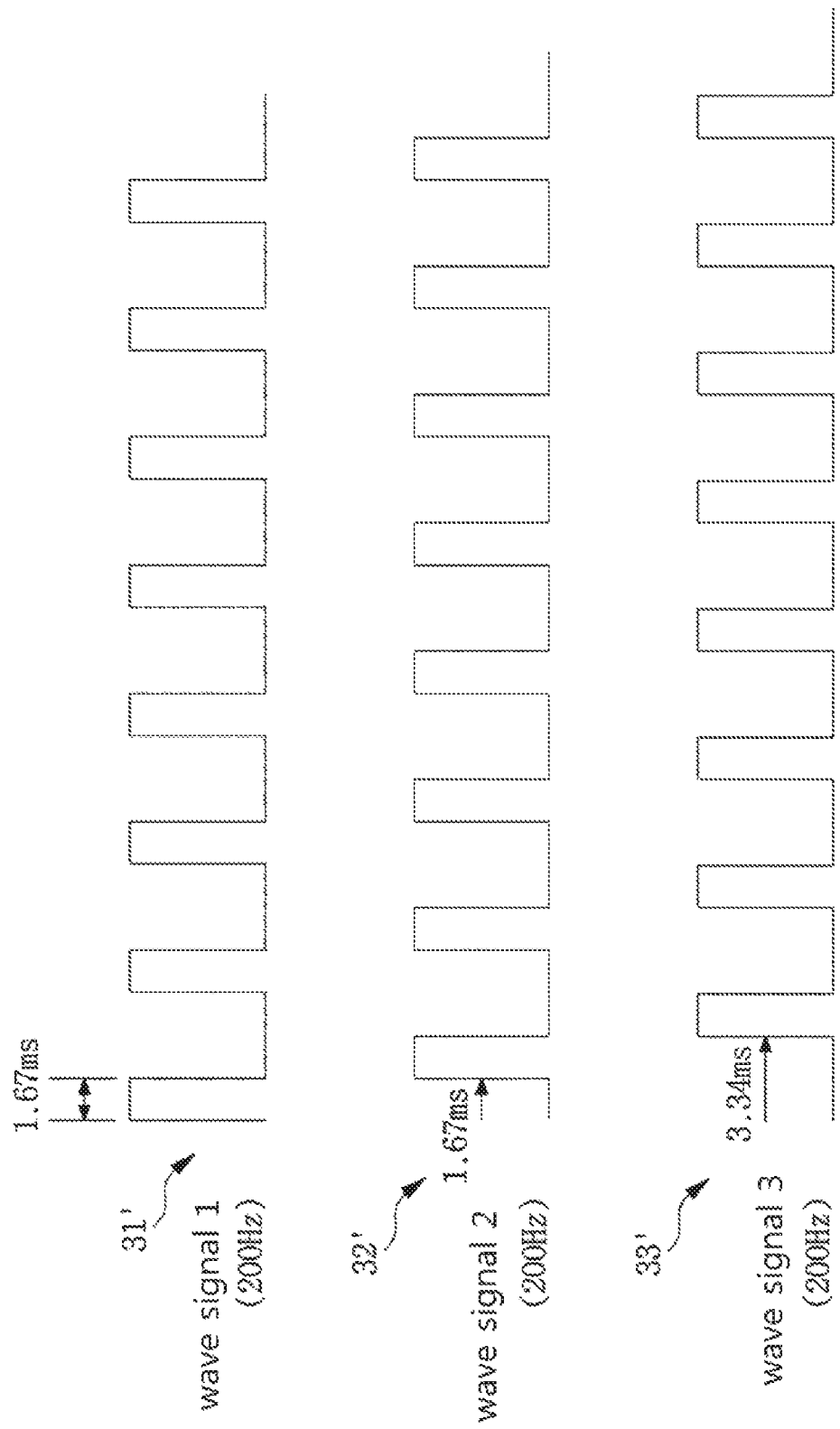

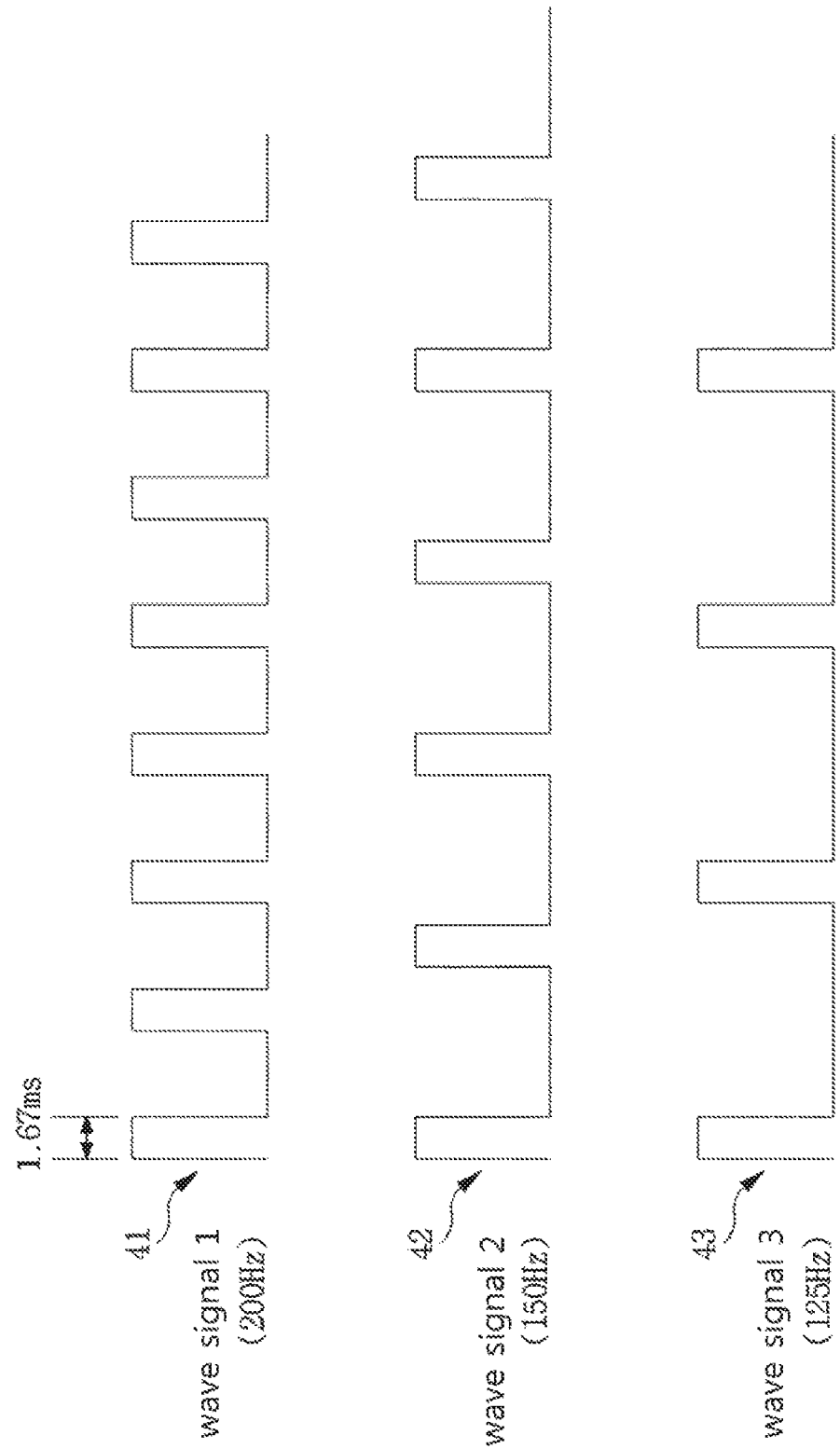

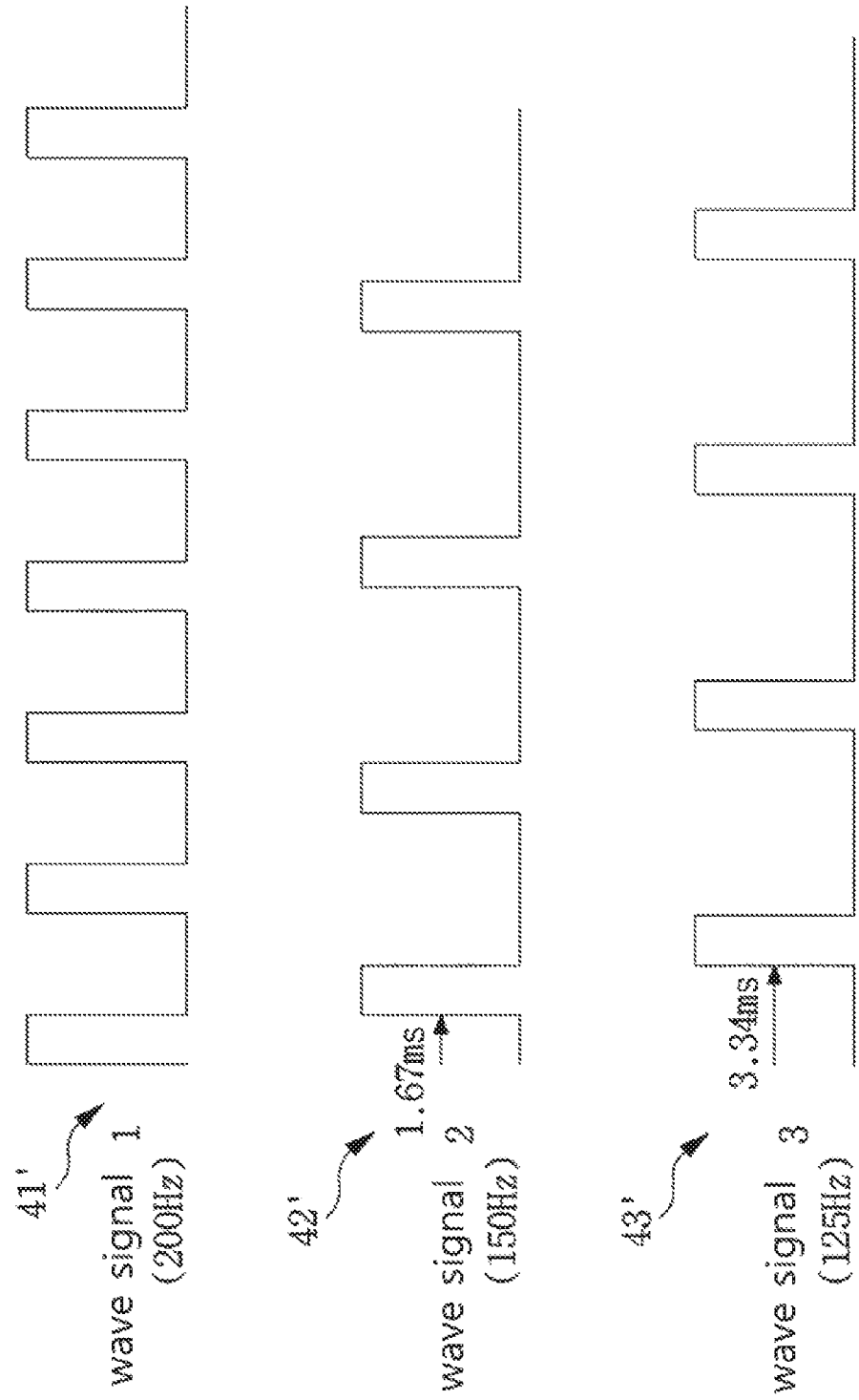

METHOD AND APPARATUS FOR GENERATING TACTILE SENSATION

CROSS REFERENCE TO RELATED APPLICATION

The present application claims priority to Korean Patent Application No. 10-2016-0155076, filed Nov. 21, 2016, the entire contents of which is incorporated herein for all purposes by this reference.

BACKGROUND OF THE INVENTION

Field of the Invention

The present disclosure generally relates to a method and an apparatus for generating a tactile sensation. More particularly, the present disclosure relates to a method and an apparatus for generating a tactile sensation in a non-contact manner.

Description of the Related Art

A tactile device provides tactile sensations by using a physical medium that delivers the tactile sensation, so the tactile device is implemented by using gloves or wristbands or implemented in a form such as an exoskeleton, etc. directly contacting with a user's body. Since contact-type tactile devices require structures and driving devices for a mechanical connection on each point of action for providing tactile sensations, configuration thereof becomes complex when a number of points of action in which independent tactile sensations are provided increases. Thereby problems such as limitation of a user's motion or vision are caused.

Accordingly, in order to solve problems of contact-type tactile devices, non-contact type tactile devices capable of transmitting tactile sensations without direct contacts between driving devices and a user's body are being studied.

The foregoing is intended merely to aid in the understanding of the background of the present disclosure, and is not intended to mean that the present disclosure falls within the purview of the related art that is already known to those skilled in the art.

SUMMARY OF THE INVENTION

Non-contact type tactile devices are capable of proving tactile sensations to a user's body without mechanical devices that interfere with movement. However, it is difficult to provide strong sensations and intensities of tactile sensations are rapidly decreased when generating a plurality of tactile sensations due to structure characteristics that deliver the tactile sensation in a non-contact environment.

Accordingly, the present disclosure has been made keeping in mind the above problems occurring in the related art, and the present disclosure is intended to provide an apparatus and a method of generating a tactile sensation in a non-contact manner, the apparatus and the method capable of generating a plurality of tactile sensations while maintaining intensities of the tactile sensation.

Another object of the present disclosure is to provide an apparatus and a method of generating a tactile sensation in a non-contact manner, the apparatus and the method capable of minimizing idleness intervals of signals that control output of the tactile sensation, and increasing output efficiency.

Still another object of the present disclosure is to provide an apparatus and a method of generating a tactile sensation in a non-contact manner, the apparatus and the method capable of efficiently modifying signals that control output of the tactile sensation while maintaining the tactile sensation that is felt by a user's body.

Technical problems obtainable from the present disclosure are non-limited by the above-mentioned technical problems, and other unmentioned technical problems may be clearly understood from the following description by those having ordinary skill in the technical field to which the present disclosure pertains.

According to one aspect of the present disclosure, there may be provided a method of generating a tactile sensation. The method may include: determining a tactile sensation information; generating a plurality of wave signals associated with each tactile sensation information; generating ultrasonic driving signals in which phases and output timings of the wave signals are adjusted based on frequencies and a number of the wave signals; and generating the tactile sensation associated with the ultrasonic driving signals.

According to another aspect of the present disclosure, there may be an apparatus for generating a tactile sensation. The apparatus may include: a tactile sensation determining unit determining a tactile sensation information; an ultrasonic driving signal generating unit generating a plurality of wave signals associated with each tactile sensation information, and generating ultrasonic driving signals in which phases and output timings of the wave signals are adjusted; and a tactile sensation generating unit generating the tactile sensation associated with the ultrasonic driving signals.

According to another aspect of the present disclosure, there may be provided software or a computer-readable medium that includes executable instructions to perform operations of expressing a tactile sensation. The executable instructions may include operations of: determining a tactile sensation information; generating a plurality of wave signals associated with each tactile sensation information; generating ultrasonic driving signals in which phases and output timings of the wave signals are adjusted based on frequencies and a number of the wave signals; and generating the tactile sensation associated with the ultrasonic driving signals.

The above briefly summarized features of the present disclosure are merely illustrative of the detailed description of the present disclosure described below and do not limit the scope of the present disclosure.

According to the present disclosure, there is provided an apparatus and a method of generating a tactile sensation in a non-contact manner in which a plurality of tactile sensations is generated while intensities thereof are maintained.

In addition, according to the present disclosure, there is provided an apparatus and a method of generating a tactile sensation in a non-contact manner in which idleness intervals of signals that control output of the tactile sensation are minimized and output efficiency is increased.

In addition, according to the present disclosure, there is provided an apparatus and a method of generating a tactile sensation in a non-contact manner in which signals that control output of the tactile sensation is efficiently modified while the tactile sensation that is felt by a user's body is maintained.

Effects obtainable from the present disclosure are non-limited by the above mentioned effect. Further, other unmentioned effects can be clearly understood from the following description by those having ordinary skill in the technical field to which the present disclosure pertains.

BRIEF DESCRIPTION OF THE DRAWINGS

The above and other objects, features and other advantages of the present disclosure will be more clearly under

FIGS. 3A and 3B are example views of wave signals processed by the ultrasonic driving signal generating unit according to the embodiment of the present disclosure;

FIGS. 4A to 4C are other example views of wave signals processed by the ultrasonic driving signal generating unit according to the embodiment of the present disclosure.

DETAILED DESCRIPTION OF THE INVENTION

Figure 1:
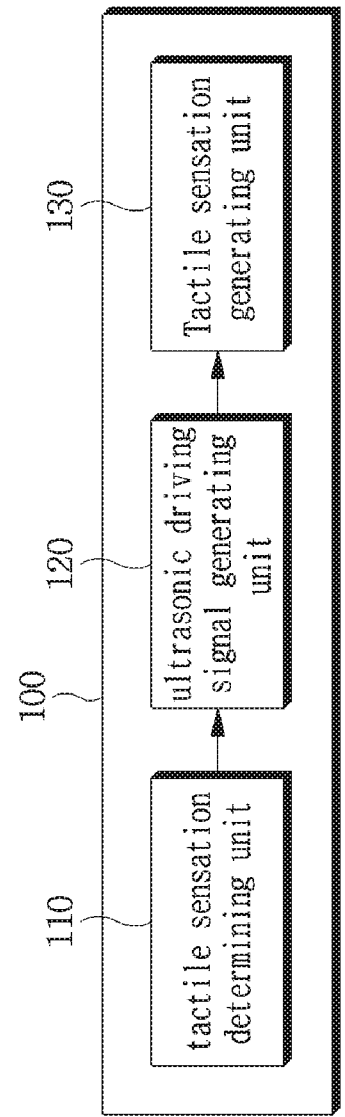
- FIG. 1 is a block diagram showing a configuration of a tactile sensation generating apparatus according to an embodiment of the present disclosure.

Hereinafter, with reference to drawings, embodiments of the present disclosure are described in detail in a manner that one of ordinary skill the art may perform the embodiments without undue difficult. However, as those skilled in the art would realize, the described embodiments may be modified in various different ways, all without departing from the spirit or scope of the present disclosure.

To avoid obscuring the subject matter of the present disclosure, while embodiments of the present disclosure are illustrated, well known functions or configurations will be omitted from the following descriptions. The drawings and description are to be regarded as illustrative in nature and not restrictive. Like reference numerals designate like elements throughout the specification.

In the present disclosure, when an element is mentioned to be "coupled" or "connected" to another element, this may mean that it is directly coupled or connected to the other element, but it is to be understood that yet another element may exist in-between. In addition, it will be understood that the terms "comprises", "comprising", "includes", "including" when used in this specification, specify the presence of one or more other components, but do not preclude the presence or addition of one or more other components unless defined to the contrary.

In the present disclosure, the terms first, second, etc. are used only for the purpose of distinguishing one element from another, and do not limit the order or importance, etc., between elements unless specifically mentioned. Therefor within the scope of the present disclosure, a first component of an embodiment may be referred to as a second component in another embodiment, or similarly, a second component may be referred to as a first component.

In the present disclosure, the components that are distinguished from each other are intended to clearly illustrate each feature and do not necessarily mean that components are separate. In other words, a plurality of components may be integrated into one hardware or software unit or one component may be distributed into plurality of hardware or software units. Thus, unless otherwise noted, such integrated or distributed embodiments are also included within the scope of the present disclosure.

In the present disclosure, the components described in the various embodiments are not necessarily essential components, and some may be optional components. Thus, embodiments including a subset of the components described in one embodiment are also included within the scope of this disclosure. Also, embodiments that include other elements in addition to those described in the various embodiments are also included within the scope of the present disclosure.

Definitions of terms that are used in the present disclosure are as follows.

A tactile sensation may include friction, stiffness, and visco-elasticity, information that indicates emotion when a person feels sensation with a tactile sense, or sensation about comprehensive texture that a user's body may feel by touching objects.

Hereinafter, with reference to drawings, embodiments of the present disclosure are described.

FIG. 1 is a block diagram showing a configuration of a tactile sensation generating apparatus according to an embodiment of the present disclosure. Referring to FIG. 1, the tactile sensation generating apparatus 100 according to the embodiment of the present disclosure may include a tactile sensation determining unit 110, an ultrasonic driving signal generating unit 120, and a tactile sensation generating unit 130.

The tactile sensation determining unit 110 may determine a property of a tactile sensation information. The property of the tactile sensation information may include information that directly controls a tactile sensation such as position, area, duration, etc. In addition, the property of the tactile sensation information may include information that may be expressed through a calculation of physical formulas such as friction, stiffness, visco-elasticity, etc. of tactile properties. Further, the property of the tactile sensation information may include information that indicates perceived tactile feelings such as roughness, sharpness, etc., or may include numerical information that represents a comprehensive texture.

The ultrasonic driving signal generating unit 120 may generate an electric signal for outputting a physical medium to output a tactile sensation associated with the property of the tactile sensation information.

The ultrasonic driving signal generating unit 120 may preset and pre-store information matching with elements (frequency, amplitude, etc.) that may represent the property of the tactile sensation information. Accordingly, the ultrasonic driving signal generating unit 120 may reference the pre-stored information, and generate ultrasonic driving signals associated with the property of the tactile sensation information that is determined by tactile sensation determining unit 110. The ultrasonic driving signal generating unit 120 may generate a plurality of wave signals that is associated with the tactile sensation. The ultrasonic driving signal generating unit 120 outputs square wave signals by modulating a plurality of sine waves having frequencies f and amplitudes A_s. However, it is not easy to output the square wave signals at an arbitrary position within the same timing, in other words, focal point. Considering this, the ultrasonic driving signal generating unit 120 may generate ultrasonic driving signals by generating a plurality of square wave signals, controlling phases of the plurality of square wave signals, and scheduling output signals.

Frequencies f of the plurality of wave signals may be determined in accordance with the tactile sensation. In addition, duty-cycles of the plurality of wave signals may be set based on a number of the wave signals and frequencies thereof. For example, active intervals of the duty-cycles of the wave signals may be set to values that are inversely proportional to the number of the wave signals and the frequencies thereof.

The ultrasonic driving signal generating unit 120 may control phases of respective wave signals when outputting the plurality of wave signals and adjust output timings of the plurality of wave signals so that each active interval of the plurality of wave signals does not overlap with each other. In addition, the ultrasonic driving signal generating unit 120 may generate ultrasonic driving signals by adjusting phases and output timings of wave signals as described above.

Further, frequencies of wave signal may variously set according to the property of the tactile sensation information. Accordingly, it is preferable for the ultrasonic driving signal generating unit 120 to set active intervals of wave signals based on a wave signal having the largest frequency value f_max. For example, active intervals of wave signals may be set to values $(1/(n*f\_max))$ that are inversely proportional to a wave signal having the largest frequency f_max among the wave signals and a number n of the wave signals.

In addition, since frequencies of wave signals may be variously set, the ultrasonic driving signal generating unit 120 may control phases of the wave signals and adjust output timings of the wave signals based on a wave signal having the largest frequency value f_max.

Further, active intervals of a plurality of wave signals may overlap even though phases thereof are controlled. Therefore, the ultrasonic driving signal generating unit 120 may adjust output timings of the plurality of wave signals considering frequency change rates thereof. The ultrasonic driving signal generating unit 120 may temporarily adjust frequencies of the plurality of wave signals for wave signals in which active intervals thereof overlap with each other so that the active intervals thereof are delayed or moved forward, thus overlapped active intervals do not occur. The ultrasonic driving signal generating unit 120 may check a difference between the temporarily adjusted frequency and an original frequency, and calculate a frequency change rate of the difference based on the original frequency. The ultrasonic driving signal generating unit 120 may adjust output timings of the plurality of wave signals considering frequency change rates that are calculated as described above. Herein, it is preferable for the ultrasonic driving signal generating unit 120 to adjust output timings of the plurality of wave signals so that calculated frequency change rates become the minimum. In addition, considering that a human body can recognize only the 20% or more of a frequency change, the ultrasonic driving signal generating unit 120 may adjust output timings of the plurality of wave signals so that calculated frequency change rates become less than 20%.

Meanwhile, the tactile sensation generating unit 130 modifies and outputs ultrasonic driving signals in ultrasonic waves. In detail, the ultrasonic driving signals may be modified and output in the ultrasonic waves by repeating contractions and extensions of the ultrasonic driving signal through a piezoelectric element. The ultrasonic waves output from the tactile sensation generating unit 130 are radiated to a user's body. Thus, a tactile sensation in a non-contact manner may be delivered to the user by using sound pressure. As described above, since the ultrasonic driving signal generating unit 120 generates ultrasonic driving signals by adjusting output timings of wave signals, idleness interval of control signals that output a tactile sensation may be minimized, and output efficiency may be increased. In addition, since the ultrasonic driving signal generating unit 120 generates ultrasonic driving signals based on frequency change rates, a plurality of wave signals may be efficiently modulated while maintaining a tactile sensation that is perceived as normal by the user's body.

Further, according to the tactile sensation generating apparatus of the present disclosure as described above, a plurality of tactile sensations may be stably generated without reduction of output intensties thereof.

Herenafter, a configuration and an operation of the ultrasonic driving signal generating unit included in the tactile sensation generating apparatus will be described in detail.

Figure 2:
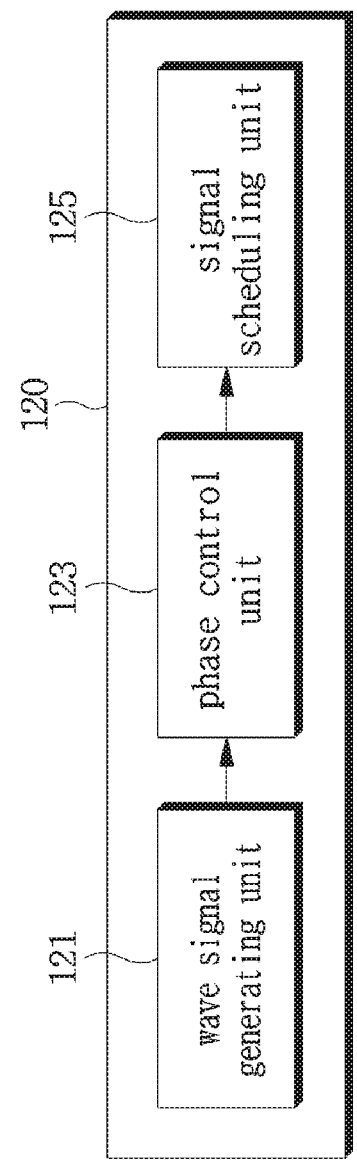
FIG. 2 is a block diagram showing a detailed configuration of an ultrasonic driving signal generating unit according to an embodiment of the present disclosure.

FIG. 2 is a block diagram showing a detailed configuration of the ultrasonic driving signal generating unit according to an embodiment of the present disclosure. Referring to FIG. 2, the ultrasonic driving signal generating unit 120 may include a wave signal generating unit 121, a phase control unit 123, and a signal scheduling unit 125.

The wave signal generating unit 121 may generate wave sgnals in which elements (frequency, amplitude (amplitude), etc.) that may represent a property of a tactile sensation are considered.

The wave signals may be generated in a number associated with a number of tactile sensations to be output. In order to generate a tactile sensation, wave signals that are based on sine waves may be generated. Although timing, in which an amplitude change occurs, of each tactile sensation physically changes, it has little influence on the user in regard to feeling the vibration since the body hardly feels the difference in phases generated by the tactile sensation. Meanwhile, a square wave includes an odd-numbered frequency component such as 3 times, 5 times, etc., and when a modulated frequency is equal to or greater than 100 Hz, a vibration perception threshold within a frequency of 3 times or more becomes high and sensitivity becomes low. Thus, if it does not have very large amplitude, it is difficult to recognize the difference from a sine wave having only an original frequency component. Considering this, the wave signal generating unit 121 may generate square wave signals obtained by performing pulse code modulation (PCM) on sine waves. Accordingly, the complexity of the wave signal generating unit 121 may be reduced since the wave signal generating unit 121 generates square wave signals.

The wave signal generating unit 121 may set amplitudes A_r and duty-cycles of wave signals based on a number of the wave signals and frequencies thereof. For example, active intervals of duty-cycles of wave signals may be set to values $(1/(n*f))$ that are inversely proportional to a number n of the wave signals and frequencies f thereof. In addition, the amplitudes A_r of the wave signals (square wave signal) may be set considering amplitudes A_s of sine waves and the number n of wave signals. Alternatively, the amplitudes A_r of the wave signals (square wave signal) may be set to values that are obtained by multiplying the amplitudes A_s of the sine waves by the number n of wave signals and by a predetermined number (for example ½). Through the above process, the wave signal generating unit 121 may set amplitudes A_r and duty-cycles of wave signals that minimize the idleness intervals therebetween and thus maximize the entire output efficiency to Further, a plurality of wave signals may include frequencies different from each other. Therefore, it is preferable for the wave signal generating unit 121 to set amplitudes A_r and duty-cycles considering frequency sizes of the plurality of wave signals. The wave signal generating unit 121 may compare frequency sizes of the plurality of wave signals, and set the amplitudes A_r and the duty-cycles based on a wave signal having the largest frequency value f_max.

The wave signal generating unit 121 may set active intervals of duty-cycles wave signals to values (1/

(n*f_max)) that are inversely proportional to the number n of wave signals and the largest frequency value f_max.

The phase control unit 123 may set phases of the plurality of wave signals so that active intervals or the plurality of wave signals are sequentially distributed. Since the active intervals of the plurality of wave signals generated by the wave signal generating unit 121 may be set to values 1/(n*f)) that are inversely proportional to the number n of the wave signals and the frequencies f thereof, the phase control unit 123 may distribute periods ((1/f) of the plurality of wave signals based on active interval timings. In other words, the phase control unit 123 may set output phases of the plurality of wave signals so that the plurality of wave signals is sequentially output.

Further, the plurality of wave signals may include frequencies different from each other, thus frequencies of the plurality of wave signals may be checked by the wave signal generating unit 121. Therefore, the phase control unit 123 receives frequency information of the plurality of wave signals from the wave signal generating unit 121, and sets output phases of the plurality of wave signals based on active intervals of the plurality of wave signals which are set to values (1/(n*f_max)) that are inversely proportional to the number n of the wave signals and the largest frequency value f_max when the plurality of wave signals includes frequencies different from each other.

The signal scheduling unit 125 may control output timings of the plurality of wave signals so that idleness intervals therebetween are minimized and the entire output efficiency is maximized. When the frequencies of the plurality of wave signals are the same, the plurality of wave signals in which phases thereof controlled does not include idleness intervals. Therefore, the signal scheduling unit 125 may receive frequency information of the plurality of wave signals from the wave signal generating unit 121, and when the frequencies of the plurality of wave signals are the same, output the plurality of wave signals as it is in which phases thereof are controlled.

Meanwhile, when the plurality of wave signals includes frequencies different from each other, the signal scheduling unit 125 may adjust output timings of the plurality of wave signals in which phases thereof are controlled to minimize idleness intervals therebetween. For example, the signal scheduling unit 125 may check frequency change rates of the plurality of wave signals in which the phases thereof are controlled, and adjust output timings of the plurality of wave signals in which the phases thereof are controlled based on a wave signal having the largest frequency change rate.

A frequency change rate at a predetermined timing t may be calculated by the formula 1 below.

$$\text{Frequency change rate} = \left| \frac{f_i - f_i(t)}{f_i} \right| * 100 \qquad \text{[Formula 1]}$$

Herein, $f_i$ indicates a frequency of an i-th wave signal, and $f_i(t)$ indicates a frequency at a predetermined timing t of the i-th wave signal.

The signal scheduling unit 125 may calculate frequency change rates as described above, adjust output timings of the plurality of wave signals based on a wave signal having the largest calculated frequency change rate, and minimize idleness intervals therebetween. For example, when frequencies $f_1$, $f_2$, and $f_3$ of the plurality of wave signals are set as $f_1$=200 Hz, $f_2$=150 Hz, and $f_3$=125 Hz, and a number n of the wave signals is 3, and the largest frequency f_max is 200 Hz. Accordingly, the wave signal generating unit 121 may set active intervals of respective wave signals to 1.67 ms, and set periods of the respective wave signals as 5 ms, 6.67 ms, and 8 ms, respectively. When respective wave signals are sequentially driven in a first period, in a second period, a first wave signal and a second wave signal may be driven in an original frequency at intervals of 5 ms and 6.67 ms, respectively. However, an active interval of the third wave signal in a second period may partially overlap with an active interval of the first wave signal in a third period. Therefore, since the second active interval of the third wave signal has an interval of 8.33 ms which is slightly delayed from 8 ms associated with 125 Hz, an output timing of the third wave signal may be scheduled by instantaneously modifying a frequency of the third wave signal to 120 Hz. In addition, an active interval of the first wave signal in a fourth period and an active interval of the second wave signal in a third period may overlap with each other within original frequencies thereof. When a driving of the first wave signal is delayed, a frequency thereof becomes 150 Hz since the instantaneous period becomes 6.67 ms. Therefore, when the driving of the first wave signal is delayed in the fourth period of the first wave signal, a frequency change rate thereof may be calculated to 25%. In addition, when a third period of the second wave signal is delayed, a frequency thereof is calculated to 120 Hz since the instantaneous period becomes 8.33 ms. Herein, a frequency change rate of the second wave signal may be calculated to 20%. Based on frequency change rates calculated as above, the signal scheduling unit 125 may schedule output timing of the second wave signal which has relatively low frequency change rate by modulating the instantaneous frequency of the second wave signal to 120 Hz in the third period interval.

In another example, the signal scheduling unit 125 may set a frequency change rate to a predetermined threshold value (for example, 20%), and may schedule output timings of a plurality of wave signals having frequency change rates less than the predetermined threshold value. For example, for wave signals in which active intervals thereof overlap with each other, frequency change rates for delaying (or moving forward) of the active intervals of respective wave signals may be checked. In addition, output timings of the wave signals may be adjusted by delaying (or moving forward) the wave signals having frequency change rates less than the predetermined threshold values.

In addition, in another embodiment, the signal scheduling unit 125 may check frequency change rates for delaying or moving forward of the wave signals, and adjust output timings of the wave signals based on a wave signal having a relatively low frequency change rate. For example, for wave signals in which active intervals thereof overlap with each other, the signal scheduling unit 125 may schedule output timings of the wave signals based on a save signal having a relatively high frequency value. In other words, an active interval of a wave signal having a relatively low frequency value is delayed more than an active interval of a wave signal having a relatively high frequency value, and a frequency change rate thereof (hereinafter, 'delayed frequency change rate') may be checked. Then, the active interval of the wave signal having the relatively low frequency value may be moved forward more than the active interval of the wave signal having the relatively high frequency value, and a frequency change rate thereof (hereinafter, 'moved forward frequency change rate') may be checked. In addition, the signal scheduling unit 125 may compare the delayed frequency change rate and the moved forward frequency change rate, and adjust output timings of the wave signals based on a wave signal having a relatively low frequency change rate value.

Figure 4C:
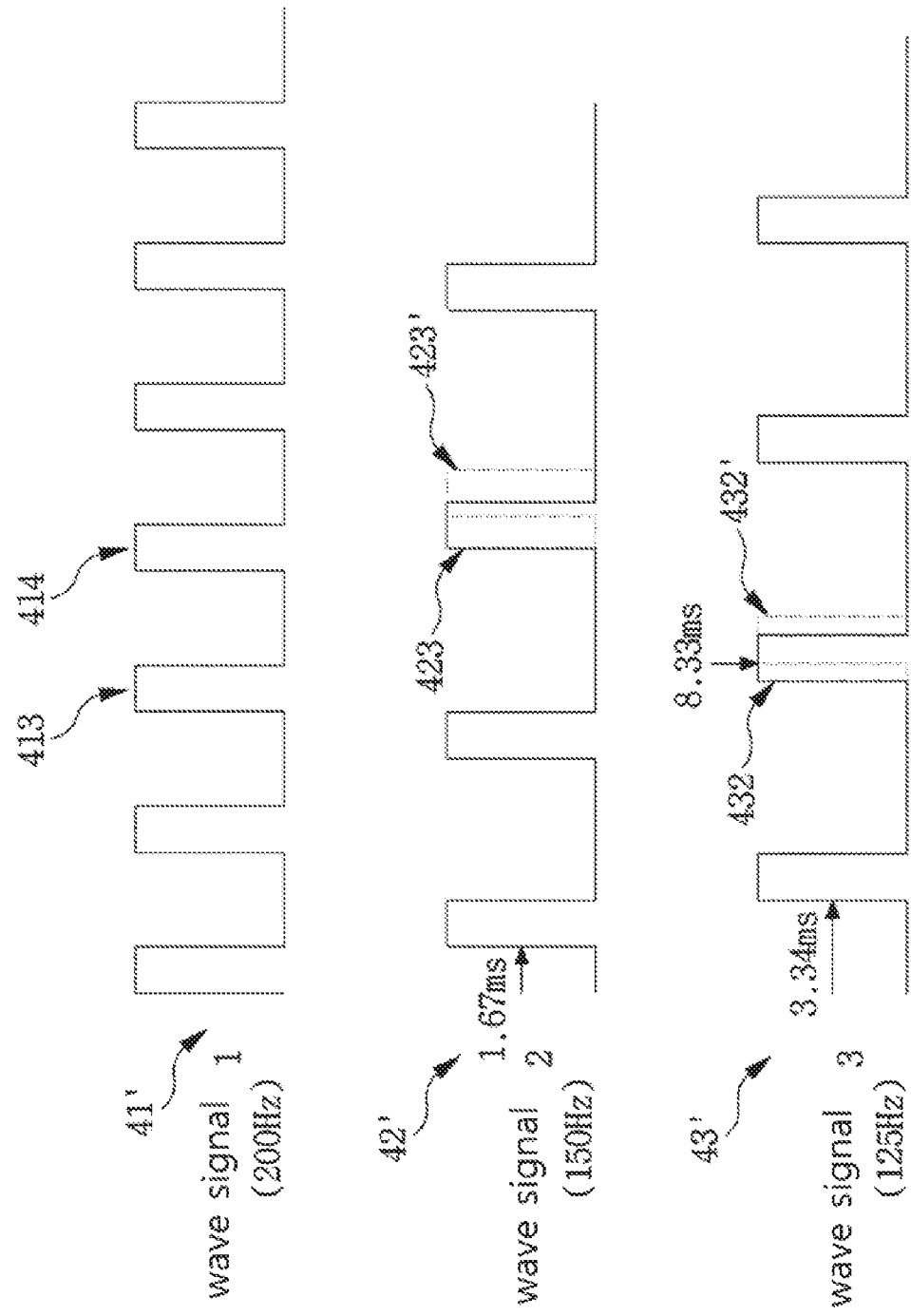

FIGS. 3A and 3B are example views of wave signals processed by the ultrasonic driving signal generating unit according to the embodiment of the present disclosure, and FIGS. 4A to 4C are other example, views of wave signals processed by the ultrasonic driving signal generating unit according to the embodiment of the present disclosure. Hereinafter, with reference to FIGS. 3A and 3B, and FIGS. 4A to 4C, an operation of the ultrasonic driving signal generating unit according to the embodiment of the present disclosure will be described.

Referring to FIG. 3A, the wave signal generating unit 121 may generate first, second, and third wave signals 31, 32, and 33 considering elements (frequency, amplitude, etc.) that may represent a property of a tactile sensation. The wave signal generating unit 121 may check the elements (frequency, amplitude, etc.) that represent the property of the tactile sensation, check that frequencies of the first, the second, and the third wave signals 31, 32, and 33 are set to the same 200 Hz, and generate square wave signals by performing pulse code modulation (PCM) on sine waves of corresponding frequencies. Based on a number (n=3) of the wave signals and the frequency (f=200 Hz), the wave signal generating unit 121 may set active intervals of the wave signals to 1.67 ms and set amplitudes A_r of the wave signals (square wave signal) to values that are obtained by multiplying amplitudes A_s of the sine waves by the number n of the wave signals and by a predetermined number (for example, ½).

Then, the phase control unit 123 may set phases of the plurality of wave signals so that active intervals of the plurality of wave signals are sequentially distributed (Refer to FIG. 3B). Since the active intervals of the plurality of wave signals generated by the wave signal generating unit 121 are set to 1.67 ms, the phase control unit 123 may control the first, the second, and the third wave signals 31, 32, and 33 to be output for each 1.67 ms unit time, and form first, second, and third wave signals 31', 32', and 33' in which phases thereof are controlled.

The signal scheduling unit 125 checks that the frequencies of the first, the second, and the third wave signals 31, 32, and 33 are set to the same frequency 200 Hz by the wave signal generating unit 121, and does not additionally schedule the first, the second, and the third wave signals 31', 32', and 33' in which phases thereof are controlled. In addition, the signal scheduling unit 125 may output the first, the second, and the third wave signals 31', 32', and 33' in which phases thereof are controlled in first, second, and third ultrasonic driving signals, respectively.

Meanwhile, referring to FIG. 4A showing other example, a plurality of wave signals may include frequencies different from each other. The wave signal generating unit 121 may check frequencies of the plurality of wave signals through information (elements (frequency, amplitude, etc.) that may represent a property of a tactile sensation) provided by the tactile sensation determining unit 110, and check whether or not the plurality of wave signals includes frequencies different from each other by comparing frequencies thereof. The wave signal generating unit 121 may check that a plurality of wave signals, for example, first, second, and third wave signals 41, 42, and 43 have frequencies of 200 Hz, 150 Hz and, 125 Hz, respectively. The wave signal generating unit 121 may generate square wave signals that are obtained by performing pulse code modulation (PCM) on respective sine waves having respective frequencies. The wave signal generating unit 121 may set active intervals of the first, the second, and the third wave signals 41, 42, and 43 to 1.67 ms based on a number of wave signals (n=3) and frequencies thereof ($f_1$=200 Hz, $f_2$=150 Hz, $f_3$=125 Hz) and based on a largest frequency (f_max=200 Hz) among the first, the second, and the third wave signals 41, 42, and 43. In addition, the wave signal generating unit 121 may set amplitudes A_r of wave signals (square wave signals) to values that are respectively obtained by multiplying amplitudes A_s of the sine waves by a number n of the wave signals and by predetermined values (for example, ½).

Then, the phase control unit 123 may set phases of the plurality of wave signals so that active intervals thereof are sequentially distributed (Refer to FIG. 4B). Since the active intervals of the plurality of wave signals generated by the wave signal generating unit 121 are set to 1.67 ms, the phase control unit 123 may form first, second, and third wave signals 41', 42', and 43' in which phases thereof are controlled so that the first, the second, and the third wave signals 41, 42, and 43 are output for each 1.67 ms unit time.

The signal scheduling unit 125 may receive frequency information ($f_1$=200 Hz, $f_2$=150 Hz, $f_3$=125 Hz) of the first, the second, and the third wave signals 41, 42, and 43 from the wave signal generating unit 121, and schedule the first, the second, and the third wave signals 41', 42', and 43' in which the phases thereof are controlled. For example, the signal scheduling unit 125 may check frequency change rates of the first, the second, and the third wave signals 41', 42', and 43' in which the phases thereof are controlled, and adjust output timings of the first, the second, and the third wave signals 41', 42', and 43' in which the phases thereof are controlled based on the maximum frequency change rate. Frequency change rates at a predetermined timing t may be calculated by using the above formula 1.

The signal scheduling unit 125 may calculate frequency change rates as described above, and adjust output timings of the first, the second, and the third wave signals 41, 42, and 43 based on the maximum frequency change rate among the calculated frequency change rates. Thus, idleness intervals therebetween may become the minimum. According to the frequencies of the first, the second, and the third wave signals 41, 42, and 43 ($f_1$=200 Hz, $f_2$=150 Hz, $f_3$=125 Hz), respective active intervals of the wave signals 41, 42, and 43 become 1.67 ms, and respective periods of the wave signals 41, 42, and 43 become 5 ms, 6.67 ms, and 8 ms. Considering this, phases of the respective wave signals 41, 42, and 43 may be controlled, and the signal scheduling unit 125 may adjust to output timings of the first, the second, and the third wave signals 41', 42', and 43' in which the phases thereof are controlled. In other words, when the respective wave signals 41', 42', and 43' are sequentially driven in a first period, the first and the second wave signals 41' and 42' are normally driven in a second period with 5 ms, 6.67 ms intervals, respectively. However, a second active interval 432 of the third wave signal 43' may partially overlap with a third active interval 413 of the first wave signal 41'. Accordingly, the signal scheduling unit 125 may schedule output timing of the third wave signal 43' by instantaneously modifying the frequency of the third wave signal 43' to 120 Hz so that the third wave signal 43' is started at 8.33 ms that is slightly later than 8 ms corresponding to 125 Hz. In addition, a fourth active interval 414 of the first wave signal 41' and a third active interval 423 of the second wave signal 42' may overlap with each other within the respective original frequencies. When a driving of the first wave signal 41' is delayed, the instantaneous period of the first wave signal 41' becomes 6.67 ms, and the frequency of the first wave signal 41' may be modified to 150 Hz, whereby the frequency change rate of the first wave signal 41' may be calculated to 25%. When a driving of the second wave signal 42' is delayed, the instantaneous period of the second wave signal 42' becomes 8.83 ms, and the frequency of the second wave signal 42' may be modified to 120 Hz. Herein, the frequency change rate of the second wave signal 42' may be calculated to 20%. Accordingly, the signal scheduling unit 125 may schedule output timing of the second wave signal 42' which has a relatively low frequency change rate than the first wave signal 41' by instantaneously modifying the frequency of the second wave signal 42' to 120 Hz at a third active interval 423'.

In another example, the signal scheduling unit 125 may preset the frequency change rates to predetermined threshold values (for example, 20%), and schedule output timings of the plurality of wave signals having frequency change rates less than the predetermined threshold value. For example, for wave signals in which active intervals thereof overlap with each other, the signal scheduling unit 125 may check frequency change rates for delays (or movements forward) of active intervals of respective wave signals, and schedule output timings of the wave signals by adjusting active intervals of the wave signals having frequency change rates less than the predetermined threshold value. As another example, for wave signals in which active intervals thereof overlap with each other, the signal scheduling unit 125 may check frequency change rates for delays (or movements forward) of active intervals of respective wave signals, and schedule output timings of the wave signals by adjusting an active interval of a wave signal having a relatively low frequency change rate.

Figure 5:
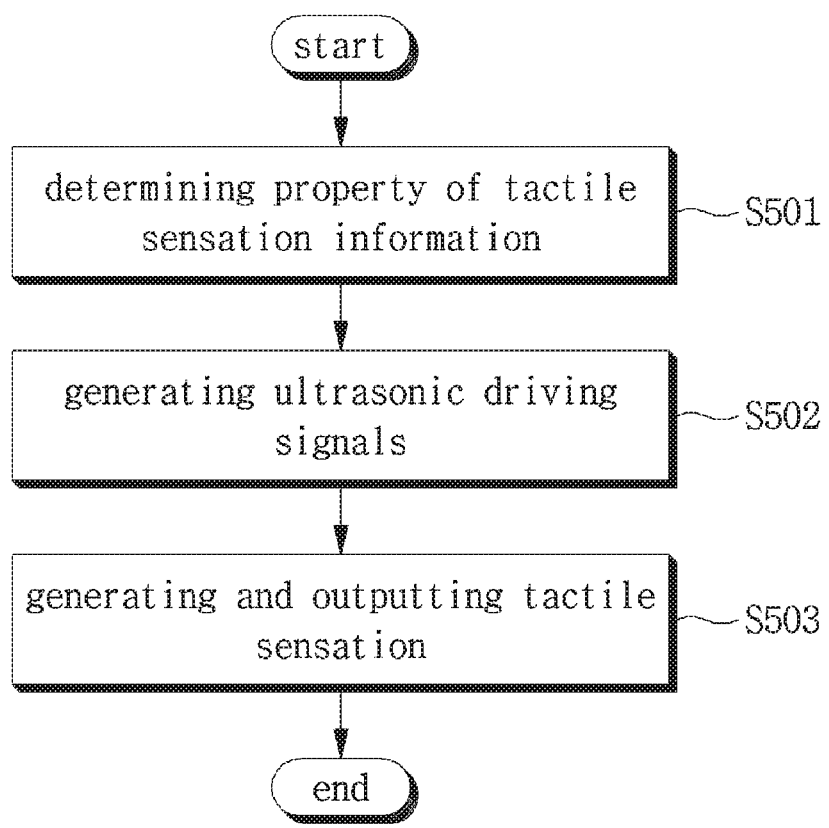
FIG. 5 is a flowchart showing a sequence of a tactile sensation generating method according to an embodiment of the present disclosure.

FIG. 5 is a flowchart showing a sequence of a tactile sensation generating method according to an embodiment of the present disclosure.

The tactile sensation generating method according to the embodiment of the present disclosure may be performed by using the tactile sensation generating apparatus according to the embodiment of the present disclosure.

First, in step S501, the tactileسsensation generating apparatus may determine a property of a tactile sensation information. For example, the property of the tactile sensation information may include information that directly controls the tactile sensation such as position, area, duration, etc. In addition, the property of the tactile sensation information may include information that may be expressed through a calculation of physical formulas such as friction, stiffness, visco-elasticity, etc. of tactile properties. Further, the property of the tactile sensation information may include information that indicates perceived tactile feelings such as roughness, sharpness, etc. or may include numerical information that represents a comprehensive texture.

Then, in step S502, the tactile sensation generating apparatus may generate ultrasonic driving signals for outputting the tactile sensation associated with the property of the tactile sensation information. For example, the tactile sensation generating apparatus may generate ultrasonic driving signals associated with the property of the tactile sensation information by using information matching with elements (frequency, amplitude, etc.) that may represent the property of the tactile sensation information.

In detail, the tactile sensation generating apparatus may generate a plurality of wave signals associated with the tactile sensation, and the plurality of wave signals may be generated based on a plurality of sine wave signals having predetermined frequencies f and amplitudes $A\_s$ Although timing, in which amplitude changes occur, of each tactile sensation physically changes, it has little influence on the user in regard to feeling the vibration since the body hardly feels the difference in phases generated by the tactile sensation. In addition, a square wave includes an odd-numbered frequency component such as 3 times, 5 times, etc., and when a modulated frequency is equal to or greater than 100 Hz, vibration perception threshold within a frequency of 3 times or more becomes high and sensitivity becomes low. Thus, if it is not very large amplitude, it is difficult to recognize the difference from a sine wave having only an original frequency component. Considering this, the tactile sensation generating apparatus may generate square wave signals obtained by performing pulse code modulation (PCM) on sine waves Accordingly, phases and output timings of the plurality of wave signals generated by the tactile sensation. generating method may be controlled by a simple configuration since the tactile sensation generating apparatus generates square wave signals.

The sensation generating apparatus may set amplitudes $A\_r$ and duty-cycles of the wave signals based on a number n of the wave signals and frequencies f thereof. Active intervals of the duty-cycles of the wave signals may be set to values that are inversely proportional to the number of the wave signals and the frequencies f thereof. In addition, the amplitudes $A\_r$ of the wave signals (square wave signals) may be set considering amplitudes $A\_s$ of sine waves and the number n of the wave signals. The amplitudes $A\_r$ of the wave signals (square wave signals) may be set to values that are obtained by multiplying the amplitudes $A\_s$ of sine waves by the number n of the wave signals and by a predetermined number (for example, ½). Through the above operations, the tactile sensation generating method may set amplitudes $A\_r$ and duty-cycles of wave signals that are capable of minimizing idleness intervals therebetween and maximizing the entire output efficiency.

Further, the plurality of wave signals may include frequencies different from each other. Accordingly, it is preferable for the tactile sensation generating method to set amplitudes $A\_r$ and duty-cycles of the plurality of wave signals considering frequency sizes thereof. The tactile sensation generating apparatus may compare frequency sizes of the plurality of wave signals, and set amplitudes $A\_r$ and duty-cycles of the plurality of wave signals based on a wave signal having the largest frequency value $f\_max$.

The tactile sensation generating apparatus may set active intervals of the duty-cycles of the wave signals to values ($1/(n*f\_max)$) that are inversely proportional to a number n of the wave signals and the largest frequency value f-max.

The tactile sensation generating apparatus may set phases of the plurality of wave signals so that set active intervals of the plurality of wave signals are sequentially distributed. Since the active intervals of the plurality of wave signals may be set to values $1/(n*f)$) that are inversely proportional to the number n of the wave signals and frequencies f thereof, the tactile sensation generating apparatus may set output phases of the plurality of wave signals by distributing periods (1/f) of the wave signals based on active interval timings so that the plurality of wave signals are sequentially output.

Further, since the plurality of wave signals may include frequencies different from each other, the tactile sensation generating apparatus may compare frequency information of the plurality of wave signals and check whether or not the plurality of wave signals include frequencies different from each other. When the plurality of wave signals include different frequencies with each other, the tactile sensation generating apparatus may set output phases of the plurality of to wave signals based on an active interval of a wave signal which is set to a value (1/ (n*f_max)) that is inversely proportional to the number n of the wave signals and the largest frequency value f_max.

In addition, in order to minimize idleness intervals therebetween and maximize the entire output efficiency, the tactile sensation generating apparatus may control output timings of the plurality of wave signals. When all frequencies of the plurality of wave signals are the same, the plurality of wave signals in which phases thereof are controlled do not include idleness intervals. Accordingly, the tactile sensation generating apparatus may compare frequency information of the plurality of wave signals and output the plurality of wave signals in which the phases thereof are controlled as it is when the all frequencies of the plurality of wave signals are the same.

Meanwhile, when the plurality of wave signals include frequencies different from each other, the tactile sensation generating apparatus may check frequency change rates of the plurality of wave signals in which phases thereof are controlled, and adjust output timing of the plurality of wave signals in which the phases thereof are controlled based on the maximum frequency change rate. A frequency change rate at a predetermined timing t may be calculated by using the above formula 1. The tactile sensation generating apparatus may minimize idleness intervals therebetween by adjusting output timings of the plurality of wave signals by using a wave signal having the maximum frequency change rate among the calculated frequency change rates. For example, when frequencies $f_1$, $f_2$, and $f_3$ of the plurality of wave signals are set to $f_1$=200 Hz, $f_2$=150 Hz, and $f_3$=125 Hz, respectively, a number n of the wave signals becomes 3, and the maximum frequency value f_max becomes 200 Hz. Accordingly, the tactile sensation generating apparatus may set active intervals of respective wave signals to 1.67 ms, and set periods of respective wave signals to 5 ms, 6.67 ms, and 8 ms. When respective wave signals are sequentially driven in a first period, the first wave signal and the second wave signal are normally driven in interval of 5 ms and 6.67 ms, respectively in a second period. However, an active interval of the third wave signal in a second period may partially overlap with an active interval of the first wave in a third period. Accordingly, since the second active interval of the third wave signal has an interval of 8.33 ms that is slightly later than 8 ms corresponding to 125 Hz, the frequency of the third wave signal is instantaneously modified to 120 Hz so that output timing of the third wave signal may be scheduled. In addition, an active interval of the first wave signal in a fourth period and an active interval of the second wave signal in a third period may overlap with each other within original frequencies thereof. When a driving of the first wave signal is delayed, the instantaneous period of the first wave signal becomes 6.67 ms and the frequency becomes 150 Hz. Accordingly, when the driving of the first wave signal is delayed in the fourth period, a frequency change rate of the first wave signal is calculated to 25%. In addition, when the third period of the second wave signal is delayed, the instantaneous period of the second wave signal becomes 8.33 ms and the frequency is calculated to 120 Hz. Herein, a frequency change rate of the second wave signal is calculated to 20%. Based on the frequency change rates calculated as described above, the tactile sensation generating unit may schedule output timings of the wave signals by instantaneously modifying the frequency of the secondsign alto wave sigal 1 to 20 Hz in the third period which has a relatively low frequency change rate.

In another example, the tactile sensation generating apparatus may set the frequency change rates to predetermined threshold values (for example, 20%), and schedule output timings of the plurality of wave signals having frequency change rates less than the predetermined threshold values. For example, for wave signals in which active intervals thereof overlap with each other, frequency change rates for delays (or movements forward) of the active intervals of respective wave signals may be checked. In addition, output timings of the wave signals may be adjusted by delaying (or movements forward) the wave signals having frequency change rates less than the predetermined threshold values.

In addition, in another embodiment, the tactile sensation apparatus may check frequency change rates for delaying or moving forward of the wave signals, and adjust output timings of the wave signals based on a wave signal having a relatively low frequency change rate. For example, for wave signals in which active intervals thereof overlap with each other, the tactile sensation generating apparatus may schedule output timing of the wave signals based on a wave signal having a relatively high frequency. In other words, an active interval of a wave signal having a relatively low frequency is delayed more than an active interval of a wave signal having a relatively high frequency, and a frequency change rate thereof (hereinafter, 'delayed frequency change rate') may be checked. Then, the active interval of the wave signal having the relatively low frequency may be moved forward more than the active interval of the wave signal having the relatively high frequency, and a frequency change rate thereof (hereinafter, 'moved forward frequency change rate') may be checked. In addition, the tactile sensation generating apparatus may compare the delayed frequency change rate and the moved forward frequency change rate, and adjust output timing of the wave signals based on a wave signal having a relatively low frequency change rate value.

Meanwhile, in step S503, the tactile sensation generating apparatus outputs the ultrasonic driving signals by modifying them to ultrasonic waves. In detail, the ultrasonic driving signals may be modified and output in the ultrasonic waves by repeating contractions and extensions of the ultrasonic driving signal through a piezoelectric element. The ultrasonic waves output from the tactile sensation generating apparatus are radiated to the user's body. Thus, a tactile sensation in a non-contact manner may be delivered to the user by using sound pressure.

The method shown in the present disclosure is described as a series of operations for clarity of description, and the order of steps is not limited. When needed, the steps may be performed at the same time or in a different order. In order to implement the method according to the present disclosure, the steps may additionally include other steps, include the remaining steps except for some steps, or may include additional steps.

The various embodiments of the disclosure are not intended to be exhaustive of all possible combinations and are intended to illustrate representative aspects of the disclosure. The matters described in the various embodiments may be applied independently or in a combination of two or more.

In addition, the embodiments of the present disclosure may be implemented by various means, for example, hardware, firmware, software, or a combination thereof. In a hardware implementation, an embodiment of the present disclosure may be implemented by one or more ASICs (Application Specific Integrated Circuits), digital signal processors (DSPs), digital signal processing devices (DSPDs), programmable logic devices (PLDs), field programmable gate arrays (FPGAs), processors, controllers, microcontrollers, microprocessors, etc.

The scope of the present disclosure includes software or machine-executable instructions (for example, an operating system, applications, firmware, programs, etc.) that enable operations the methods according to the various embodiments to be performed on a device or computer, and a non-transitory computer-readable medium in which such software or instructions are stored and are executable on a device or computer.

What is claimed is:

1. A method of generating a tactile sensation, the method comprising:
   determining a plurality of non-contact type tactile sensation information;
   generating a plurality of wave signals associated with each non-contact type tactile sensation information;
   generating ultrasonic driving signals in which phases and output timings of the wave signals are adjusted based on frequencies and a number of the wave signals; and
   generating the non-contact type tactile sensation associated with the ultrasonic driving signals on a mid-air space of a device,
   wherein the generating ultrasonic driving signals comprises controlling phases of respective wave signals and adjusting output timings of the plurality of wave signals so that each active interval of the plurality of wave signals does not overlap with each other.

2. The method of claim 1, wherein the generating of the wave signals includes setting duty-cycles for the plurality of wave signals having the same frequency considering the number of the wave signals.

3. The method of claim 1, wherein the generating of the wave signals includes setting duty-cycles for the plurality of wave signals having frequencies different from each other considering the number of the wave signals and based on a wave signal having the largest frequency value.

4. The method of claim 3, wherein the generating of the ultrasonic driving signals includes controlling phases and frequencies of the wave signals based on a human sensitivity of on the frequencies in order to minimize a cognitive distortion.

5. The method of claim 3, wherein in the generating of the ultrasonic driving signals, output timings of the plurality of wave signals are scheduled so that frequency change rates thereof become a minimum.

6. The method of claim 3, wherein in the generating of the ultrasonic driving signals, output timings of the plurality of wave signals are scheduled so that frequency change rates thereof become equal to or less than a predetermined threshold value.

7. The method of claim 3, wherein in the generating of the ultrasonic driving signals, the plurality of wave signals are scheduled based on the wave signal having a relatively high frequency value.

8. The method of claim 3, wherein in the generating of the ultrasonic driving signals, amplitudes of the ultrasonic driving signals are set to be proportional to a frequency of the wave signal having the largest frequency value, and to a number of the ultrasonic driving signals.

9. An apparatus for generating a tactile sensation, the apparatus comprising:
   a non-contact type tactile sensation determining unit determining a plurality of non-contact type tactile sensation information;
   an ultrasonic driving signal generating unit generating a plurality of wave signals associated with each non-contact type tactile sensation information, and generating ultrasonic driving signals in which phases and output timings of the wave signals are adjusted; and
   a non-contact type tactile sensation generating unit generating the non-contact type tactile sensation associated with the ultrasonic driving signals,
   wherein the ultrasonic driving signal generating unit controls phases of respective wave signals and adjusts output timings of the plurality of wave signals so that each active interval of the plurality of wave signals does not overlap with each other.

10. The apparatus of claim 9, wherein the ultrasonic driving signal generating unit controls phases and frequencies of the wave signals based on a sensitivity of a human sensitivity of on the frequencies in order to minimize a cognitive distortion.

11. The apparatus of claim 9, wherein the ultrasonic driving signal generating unit sets duty-cycles for the plurality of wave signals having frequencies different from each other considering a number of the wave signals and based on a wave signal having the largest frequency value, and controls phases of the plurality of wave signals based on the wave signal having the largest frequency value.

12. The apparatus of claim 11, wherein the ultrasonic driving signal generating unit schedules output timings of the plurality of wave signals so that frequency change rates thereof become a minimum.

13. The apparatus of claim 11, wherein the ultrasonic driving signal generating unit schedules output timings of the plurality of wave signals so that frequency change rates thereof become equal to or less than a predetermined threshold value.

14. The apparatus of claim 11, wherein the ultrasonic driving signal generating unit schedules the plurality of wave signals based on the wave signal having a largest frequency value.

15. The apparatus of claim 9, wherein the ultrasonic driving signal generating unit includes:
   a wave signal generating unit generating the plurality of wave signals in which frequencies thereof are set associated with the tactile sensation, and amplitudes and duty-cycles thereof are set considering a number of tactile sensations;
   a phase control unit adjusting phases of the plurality of wave signals; and
   a signal scheduling unit adjusting output timings of the plurality of phase-adjusted wave signals.

16. The apparatus of claim 15, wherein the phase control unit adjusts the phases of the wave signals considering the frequencies and the duty-cycles of the wave signals.

17. The apparatus of claim 15, wherein the phase control unit controls phases of the plurality of wave signals having frequencies different from each other based on a wave signal having the largest frequency value.

18. The apparatus of claim 17, wherein the signal scheduling unit schedules the plurality of wave signals so that frequency change rates thereof become a minimum.

19. The apparatus of claim 17, wherein the signal scheduling unit schedules the plurality of wave signals so that frequency change rates thereof become equal to or less than a predetermined threshold value.

20. The apparatus of claim 11, wherein the signal scheduling unit schedules the plurality of wave signals based on a phase of a wave signal having the largest frequency value.

* * * * *